United States Patent
Green (10) Patent No.: US 9,572,515 B1
(45) Date of Patent: Feb. 21, 2017

(54) CONTOURED QUADRATURE COIL ARRANGEMENT

(71) Applicant: Fonar Corporation, Melville, NY (US)

(72) Inventor: Charles A. Green, Holbrook, NY (US)

(73) Assignee: Fonar Corporation, Melville, NY (US)

(*) Notice: Subject to any disclaimer, the term of this patent is extended or adjusted under 35 U.S.C. 154(b) by 255 days.

(21) Appl. No.: 14/208,974

(22) Filed: Mar. 13, 2014

Related U.S. Application Data (60) Provisional application No. 61/778,855, filed on Mar. 13, 2013.

(51) Int. Cl.
| | |
|---|---|
| *A61B 5/055* | (2006.01) |
| *G01R 33/34* | (2006.01) |
| *A61B 5/05* | (2006.01) |
| *G01R 33/341* | (2006.01) |
| *G01R 33/3415* | (2006.01) |
| *G01R 33/44* | (2006.01) |
| *G01R 33/00* | (2006.01) |

(52) U.S. Cl.
CPC ............ *A61B 5/055* (2013.01); *A61B 5/0555* (2013.01); *G01R 33/34* (2013.01); *G01R 33/34046* (2013.01); *A61B 5/05* (2013.01); *G01R 33/0005* (2013.01); *G01R 33/341* (2013.01); *G01R 33/3415* (2013.01); *G01R 33/441* (2013.01)

(58) Field of Classification Search
None
See application file for complete search history.

(56) References Cited

U.S. PATENT DOCUMENTS

| | | | |
|---|---|---|---|
| 4,918,388 A * | 4/1990 | Mehdizadeh | .... G01R 33/34046 324/322 |
| 6,335,623 B1 | 1/2002 | Damadian et al. | |
| 6,414,490 B1 | 7/2002 | Damadian et al. | |
| 6,677,753 B1 | 1/2004 | Danby et al. | |
| 7,701,209 B1 * | 4/2010 | Green | .................. G01R 33/307 324/307 |
| 2008/0211498 A1 * | 9/2008 | Dannels | ........... G01R 33/34007 324/309 |

* cited by examiner

*Primary Examiner* — Katherine Fernandez
*Assistant Examiner* — Michael Kellogg
(74) *Attorney, Agent, or Firm* — Lerner, David, Littenberg, Krumholz & Mentlik, LLP (57) ABSTRACT

An apparatus for magnetic resonance imaging includes a magnet, a patient support, and a contoured quadrature coil. The contoured quadrature coil includes a ring coil and an angled butterfly coil. The angled butterfly coil may have a front outer section, an inner section, and a back outer section. The front outer section and the back outer section may be oriented diagonally from the plane of the ring coil such that a portion of the front outer section and/or the back outer section are disposed above the plane of the ring coil and a portion of the front outer section and/or the back outer section are disposed below the plane of the ring coil. Thus, the planes of the front and back outer sections may be angled with respect to each other, and the inner section may be substantially pyramidal and disposed along or below the plane of the ring coil.

16 Claims, 4 Drawing Sheets

CONTOURED QUADRATURE COIL ARRANGEMENT

CROSS-REFERENCE TO RELATED APPLICATIONS

The present application claims the benefit of the filing date of U.S. Provisional Patent Application No. 61/778,855 filed Mar. 13, 2013, the disclosure of which is hereby incorporated herein by reference.

TECHNICAL FIELD

The present disclosure relates to a magnetic resonance imaging apparatus and procedures for imaging the lower abdominal region of a subject. In particular, the present disclosure provides a magnetic resonance imaging apparatus having a contoured quadrature coil arrangement for imaging a lower portion of a patient.

BACKGROUND

In magnetic resonance imaging, an object to be imaged such as, for example, a body of a human subject, is exposed to a strong, substantially constant static magnetic field. Radio frequency excitation energy is applied to the body, and this energy causes the spin vectors of certain atomic nuclei within the body to rotate or "precess" around axes parallel to the direction of the static magnetic field. The precessing atomic nuclei emit weak radio frequency signals during the relaxation process, referred to herein as magnetic resonance signals. Different tissues produce different signal characteristics. Furthermore, relaxation times are a major factor in determining signal strength. In addition, tissues having a high density of certain nuclei will produce stronger signals than tissues with a low density of such nuclei. Relatively small gradients in the magnetic field are superimposed on the static magnetic field at various times during the process so that magnetic resonance signals from different portions of the patient's body differ in phase and/or frequency. If the process is repeated numerous times using different combinations of gradients, the signals from the various repetitions together provide enough information to form a map of signal characteristics versus location within the body. Such a map can be reconstructed by conventional techniques well known in the magnetic resonance imaging art, and can be displayed as a pictorial image of the tissues as known in the art.

The magnetic resonance imaging technique offers numerous advantages over other imaging techniques. MRI does not expose either the patient or medical personnel to X-rays and offers important safety advantages. In addition, magnetic resonance imaging can obtain images of soft tissues and other features within the body which are not readily visualized using other imaging techniques. Accordingly, magnetic resonance imaging has been widely adopted in the medical and allied arts.

Several factors impose significant physical constraints in the positioning of patients and ancillary equipment in MRI imaging. Many MRI magnets use one or more solenoidal superconducting coils to provide the static magnetic field arranged so that the patient is disposed within a small tube running through the center of the magnet. The magnet and tube typically extend along a horizontal axis, so that the long axis or head-to-toe axis of the patient's body must be in a horizontal position during the procedure. Moreover, equipment of this type provides a claustrophobic environment for the patient. Iron core magnets have been built to provide a more open environment for the patient. These magnets typically have a ferromagnetic frame with a pair of ferromagnetic poles disposed one over the other along a vertical pole axis with a gap between them for receiving the patient. The frame includes ferromagnetic flux return members such as plates or columns extending vertically outside of the patient-receiving gap. A magnetic field is provided by permanent magnets or electromagnetic coils associated with the frame. A magnet of this type can be designed to provide a more open environment for the patient. However, it is still generally required for the patient to lie with his or her long axis horizontal.

Recently, ferromagnetic frame magnets having horizontal pole axes have been developed. As disclosed, for example, in commonly assigned U.S. patent application Ser. No. 08/978,084, filed on Nov. 25, 1997, and U.S. Pat. Nos. 6,414,490 and 6,677,753, the disclosures of which are incorporated by reference herein, a magnet having poles spaced apart from one another along a horizontal axis provides a horizontally oriented magnetic field within a patient-receiving gap between the poles. Such a magnet can be used with a patient-positioning device including elevation and tilt mechanisms to provide extraordinary versatility in patient positioning. For example, where the patient positioning device includes a bed or similar device for supporting the patient in a recumbent position, the bed can be tilted and/or elevated so as to image the patient in essentially any position between a fully standing position and a fully recumbent position, and can be elevated so that essentially any portion of the patient's anatomy is disposed within the gap in an optimum position for imaging. As further disclosed in the previously mentioned applications, the patient positioning device may include additional elements such as a platform projecting from the bed to support the patient when the bed is tilted towards a standing orientation. Still other patient supporting devices can be used in place of a bed in a system of this type. For example, a seat may be used to support a patient in a sitting position. Thus, magnets of this type provide extraordinary versatility in imaging.

Another physical constraint on MRI imaging has been posed by the requirements for RF antennas to transmit the RF excitation energy and to receive the magnetic resonance signals from the patient. The antenna that receives the signals is positioned near that portion of the patient's body that is to be imaged so as to maximize the signal-to-noise ratio and improve reception of the weak magnetic resonance signals. The antenna that applies RF excitation energy can be positioned in a similar location to maximize efficiency of the applied RF energy. In some cases, the same antenna is used to apply RF excitation energy and to receive the magnetic resonance signals at different times during the process. However, it is often desirable to provide two separate antennas for this purpose.

The antennas are typically formed as one or more loops of electrically conductive material. Such a loop antenna must be positioned so that the conductor constituting the loop extends along an imaginary plane or surface having a normal vector transverse to the direction of the static magnetic field. Stated another way, the antenna must be arranged to transmit or receive electromagnetic fields in a direction perpendicular to the direction of the static magnetic field if it is to interact with the precessing atomic nuclei. This requirement has further limited available antenna configurations and techniques. For example, in a vertical-field magnet such as a ferromagnetic frame magnet having a vertical pole axis, it is impossible to use a loop antenna with the loop disposed generally in a horizontal plane below the body of a recumbent patient. Such an antenna has a normal vector which is vertical and hence parallel to the direction of the static magnetic field. A loop antenna which encircles the patient with its normal vector extending horizontally can be employed. Also, planar or saddle-shaped loops extending in generally vertical planes or surfaces, and having normal vectors in the horizontal direction transverse to the long axis of the patient can be positioned on opposite sides of the patient. However, these antenna configurations do not provide optimum signal-to-noise ratios in some procedures as, for example, in imaging the spine, head or pelvic region.

More recently, quadrature coil arrangements having a combination of planar coil antenna have also been developed. As disclosed, for example, in commonly assigned U.S. Pat. No. 7,701,209, issued on Apr. 20, 2010 to Charles A. Green (hereinafter, the '209 Patent), the disclosure of which is incorporated by reference herein in its entirety, two planar coil antenna are combined in the seat and/or back of a chair that defines a support for a patient. In one example, the coil arrangement consists of a substantially flat butterfly receiver coils arranged in a quadrature mode. First and second coils with perpendicular coil vectors lie in a substantially parallel plane that is parallel to surface of the patient support.

In another example, a quadrature planar coil antenna assembly includes a loop coil antenna and a butterfly coil antenna mounted to a support using a plurality of mounting members. The coil vector of the loop coil antenna is perpendicular to the surface of the support, and the coil vector of the butterfly coil is parallel to the surface of the support. The antenna of the second example is vertically adjustable along the support to allow for imaging of the spine, heart, or other areas of the torso, and may also be adjusted to allow a patient to sit on the antenna so that images of the lower abdomen, e.g., pelvic region or prostate, can be obtained.

However, imaging performed using the previously disclosed quadrature coil arrangements is subject to several limitations. For example, due to the substantially planar configuration of each of the coils, it is necessary to place the target imaging area of the patient as close as possible to the coil in order to produce a higher quality magnetic resonance image. Generally, the target imaging area for a patient is separated from the coils by layers of skin, tissue, and fat. The amount of the separation may vary depending on the physique of a given patient. As such, the quality of images taken using the above described coils have a high variance of quality and, in general, are of low quality.

For further example, imaging of a patient's prostate is still generally performed using an RF coil that inserted into the patient. Such techniques are generally uncomfortable and unpleasant. As such, there is a great demand for an apparatus and method for imaging a patient that is less intrusive while yielding high quality (e.g., high-resolution) results.

BRIEF SUMMARY

In one embodiment, this disclosure provides an apparatus that for magnetic resonance imaging that may include a magnet defining a patient receiving space and having a static magnetic field with a field vector in a substantially horizontal direction, a patient support configured to support a patient in the patient receiving space, said patient support further comprising a padded upper surface configured to receive a sitting patient, and a contoured quadrature coil antenna arrangement for receiving a signal from a patient disposed within the patient receiving space. The contoured quadrature coil antenna arrangement may be affixed to the patient support and include a first antenna that is oriented parallel to an upper surface of the patient support, the first antenna being substantially planar and substantially circular and a second antenna having a front outer section, an inner section, and a back outer section, the front outer section being oriented diagonally from the plane of the first antenna such that a portion of the front outer section is disposed above the plane of the first antenna and a portion of the front outer section is disposed below the plane of first antenna, the back outer section being oriented diagonally from the plane of the first antenna such that a portion of the back outer section is disposed above the plane of the first antenna and a portion of the back outer section is disposed below the plane of first antenna, wherein the planes of the front and back outer sections are angled with respect to each other, and the inner section being substantially pyramidal and disposed along or below the plane of the first antenna.

In another embodiment of the apparatus, the first antenna has a first coil vector, the second antenna has a second coil vector, and the first coil vector and the second coil vector are transverse with respect to the field vector of the magnet.

In a further embodiment of the apparatus, the contoured quadrature coil arrangement is disposed within a plane perpendicular to a horizontal axis of the static magnetic field.

In yet another embodiment of the apparatus, the apparatus may include an elevator for raising and lower said patient support relative to said magnet while the patient support is holding the patient in an upright orientation so as to position any part of the patient within said patient-receiving space.

In yet a further embodiment of the apparatus, the second antenna comprises a plurality of discontinuous segments.

In another embodiment of the apparatus, the discontinuous segments may include a central segment corresponding to the inner section of the second antenna, and a plurality of outer segments, the plurality of outer segments corresponding to the front outer section and the back outer section of the second antenna.

In a further embodiment of the apparatus, the central segment is discontinuous and comprises a front segment and a back segment.

In yet another embodiment of the apparatus, the second antenna comprises a plurality of segments so as to be continuous.

This disclosure also provides for a contoured quadrature coil antenna arrangement that may include a first antenna that is oriented parallel to an upper surface of a patient support, the first antenna being substantially planar and substantially circular, and a second antenna having a front outer section, an inner section, and a back outer section, the front outer section being oriented diagonally from the plane of the first antenna such that a portion of the front outer section is disposed above the plane of the first antenna and a portion of the front outer section is disposed below the plane of first antenna, the back outer section being oriented diagonally from the plane of the first antenna such that a portion of the back outer section is disposed above the plane of the first antenna and a portion of the back outer section is disposed below the plane of first antenna, wherein the planes of the front and back outer sections are angled with respect to each other, and the inner section being substantially pyramidal and disposed along or below the plane of the first antenna.

In another embodiment of contoured quadrature coil antenna arrangement, the first antenna may have a first coil vector, the second antenna has a second coil vector, and the first coil vector and the second coil vector may be transverse with respect to a horizontal field vector of a magnet.

In a further embodiment of the contoured quadrature coil antenna arrangement, the contoured quadrature coil arrangement may be disposed within a plane perpendicular to a horizontal axis of a static magnetic field emitted by a magnet.

In yet another embodiment of the contoured quadrature coil antenna arrangement, the contoured quadrature coil arrangement may be disposed within an enclosure mounted to an elevator for raising and lower a patient support relative to a magnet while the patient support is holding a patient in an upright orientation so as to position any part of the patient within said patient-receiving space.

In yet a further embodiment of the contoured quadrature coil antenna arrangement the second antenna may include a plurality of discontinuous segments.

In another embodiment of the contoured quadrature coil antenna arrangement, the discontinuous segments may include a central segment corresponding to the inner section of the second antenna, and a plurality of outer segments, the plurality of outer segments corresponding to the front outer section and the back outer section of the second antenna.

In a further embodiment of the contoured quadrature coil antenna arrangement, the central segment may be discontinuous and may include a front segment and a back segment.

In yet another embodiment of the contoured quadrature coil antenna arrangement the second antenna may include a plurality of segments so as to be continuous.

DETAILED DESCRIPTION

The present disclosure provides magnetic resonance imaging using a contoured quadrature coil that includes a loop coil and an angled butterfly coil. In accordance with this arrangement, high quality magnetic images of the pelvic region may be advantageously obtained for both male and female patients, when such patients are preferably positioned in an upright position.

Figure 1:
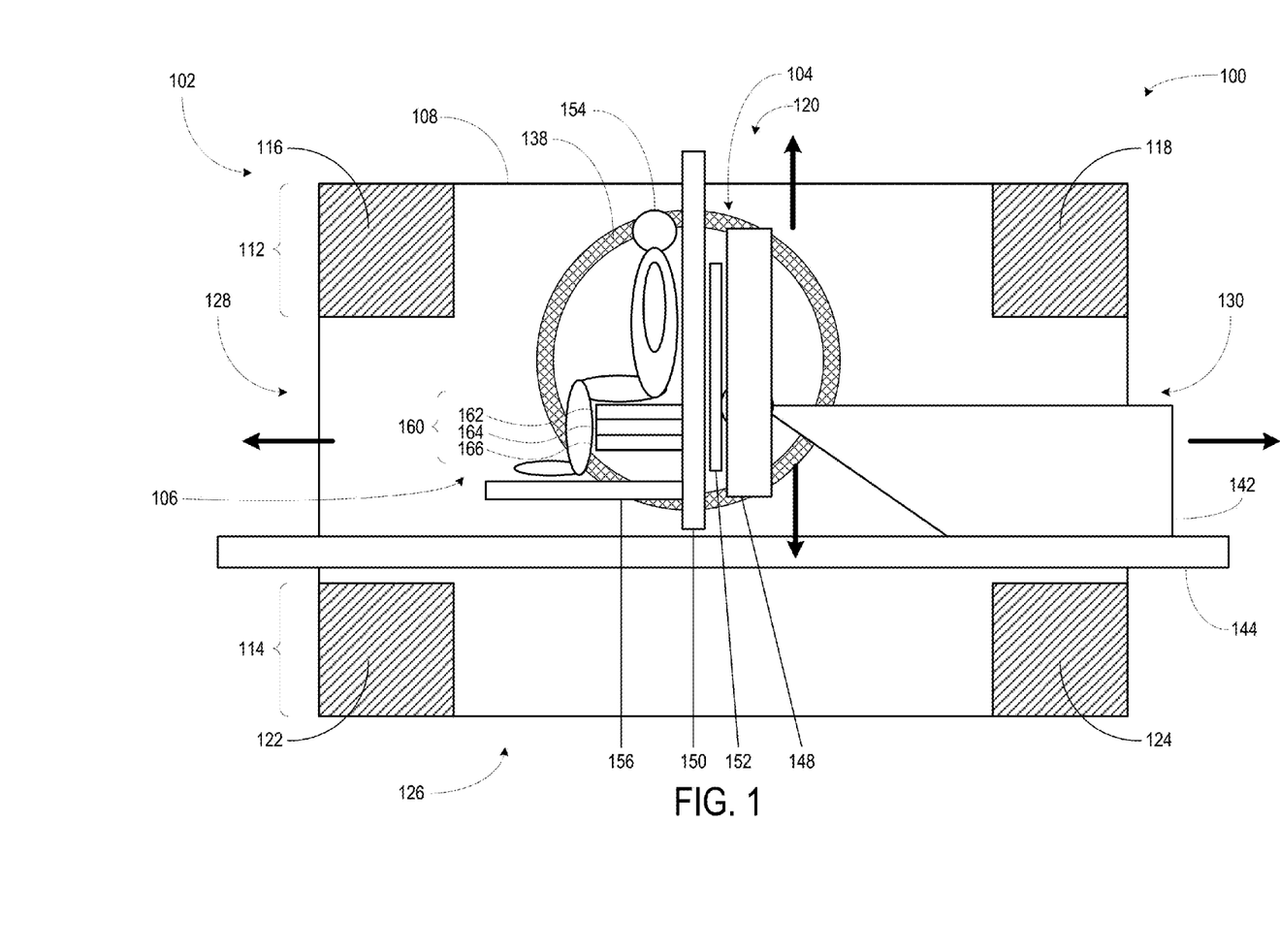
FIG. 1 illustrates an exemplary MRI apparatus for imaging a subject according to aspects of the disclosure.

FIG. 1 illustrates an exemplary MRI apparatus 100 for imaging a subject according to aspects of the disclosure. In one embodiment, the MRI apparatus 100 includes a magnet having a ferromagnetic frame 102, a magnetic flux generator 104, and a patient handling system 106. The ferromagnetic frame 102 includes a first side wall 108 and a second side wall. The side walls extend vertically. As FIG. 1 is a sectional view of the MRI apparatus 100, FIG. 1 does not show the second side wall or any of its associated structures for clarity.

The ferromagnetic frame 102 may also include a top flux return structure 112 and a bottom flux return structure 114.

The top flux return structure 112 may include two columnar structures 116 and 118. Between these two columnar structures, a top opening 120 is defined. Similarly, the bottom flux return structure 114 may include two columns 122 and 124 that together define a bottom opening 126. Thus, the side walls and the flux return members 112 and 114 form a rectilinear structure, with the top flux return structure 112 constituting the top wall of the rectilinear structure, the bottom flux return structure 114 constituting the bottom wall of the rectilinear structure and the side walls forming the side walls of the rectilinear structure. The frame 102 defines a front patient opening 128 on one side of the frame and a similar back patient opening 130 on the opposite side of the frame.

The ferromagnetic frame further includes a first magnetic pole and a second magnetic pole. The first magnetic pole extends from the first side wall 108 towards the second side wall and the second magnetic pole extends from the second side wall towards the first side wall 108. The magnetic poles are generally cylindrical and are coaxial with one another on a common horizontal polar axis. Between the magnetic poles is a gap accessed by the front patient opening 128, the back patient opening 130, the top opening 120 or the bottom opening 126.

The magnetic flux generator 104 includes a first electromagnetic coil assembly 138 magnetically coupled to ferromagnetic frame 102, proximate to side 108, and parallel to side 108. The magnetic flux generator 104 also includes a second electromagnet coil assembly (not shown) magnetically coupled to ferromagnetic frame 102, proximate to the second side wall, and parallel to the second side wall. As previously noted, these electromagnetic coil assemblies 138 and 140 may be either resistive or superconductive. Alternatively, the magnetic flux generator 104 may be a permanent magnet. The magnetic flux generator 104 may be configured to emit a magnetic field B0 along one or more axes. The magnetic flux generator 104 may also include one or more gradient coils (not shown) for inducing a gradient in the $B_0$ magnetic field.

The apparatus 100 may further include a patient support assembly 106 including a chair or bench on which a patient is capable of sitting. The patient handling system 106 is capable of three degrees of motion. The patient handling system further supports positioning of a patient in the Trendelburg and reverse-Trendelburg orientations. Generally, the degrees of motion allow for positioning of the patient in a variety of orientations or positions. The patient handling system 106 may include a carriage 142 mounted on rails 144. The carriage 142 may move linearly back and forth along the rails 144. The rails 144 typically do not block the bottom open space 126.

A generally horizontal pivot axis is mounted on carriage 142. An elevator frame 148 is mounted to the pivot axis. The carriage 142 is operable to rotate the elevator frame 148 about the pivot axis. A patient support 150 is mounted on the elevator frame 148. The patient support 150 may be moved linearly along the elevator frame 148 by an actuator 152. Thus, a patient 154 can be positioned with a total of three degrees of freedom, or along three axes of movement. Specifically, the patient handling system 106 can move a patient 154 in two linear directions and also rotate patient 154 around an axis. The solid black arrows of FIG. 1 show various axes of movement possible with the patient handling system 106. Note that often the rails 108 are mounted such that portions of patient 154 may be positioned below the rails through bottom open space 126.

The apparatus 100 may further include a novel quadrature coil arrangement including a loop coil antenna and a butterfly antenna. Unlike previously disclosed quadrature coil arrangements, which are substantially flat or planar, the novel arrangement of the present disclosure is effectively contoured (i.e., not substantially flat). The contours provide for the magnetic field generated above the coils (i.e., where the patient is positioned) to extend further above the coils and permit imaging of locations from a greater distance away. In other words, because the disclosed quadrature coil is contoured, or angled, it can be placed closer to the subject being imaged and thusly, better detect resonance signals emitted from excited nuclei within the subject.

Accordingly, the patient support assembly 106 may include a seat assembly 160 having the disclosed quadrature coil arrangement. In particular, the seat assembly 160 includes a seat or setting surface 166, an enclosure 162 containing the contoured quadrature coil, and a cushion 164. In accordance with this illustrative embodiment, enclosure 162, which is shown as being adjacent to patient 154, contains the contoured quadrature coil having a normal vector transverse to the horizontal pole axis of the magnetic poles of the MRI apparatus 100, and thus transverse to the magnetic field vector parallel to the horizontal pole axis.

The contoured quadrature coil arrangement of the present disclosure may be useful for imaging any portion of a patient's lower abdominal region. For example, the contoured quadrature coil arrangement may be used for imaging the patient's prostate, pelvic floor, or other anatomy local to the prostate and/or pelvic floor. For example, in both female and male patients, the rectum or urinary bladder may be advantageously imaged. For female patients, the uterus and ovaries may also be advantageously imaged. In addition, gravity brings the region of interest closer to the contoured quadrature coil so as to further minimize distance between the pelvic region and the contoured quadrature coil and further optimizes the quality of the images obtained.

Additionally, the shape of the coil arrangement of the present disclosure is selected to be universally acceptable to a patient's anatomy. In other words, due to the open-air nature of the coil arrangement (i.e., all the patient needs to do is sit on the coil), any patient is capable of being imaged using the same coil. Furthermore, because of the unique shape of the coil arrangement, a relatively more uniform level of image quality is achieved for all patients, despite varying physiques of different patients.

Unlike previously disclosed coil arrangements, the coil arrangement of the present disclosure is capable of imaging the target anatomy (e.g., prostate, pelvic floor, etc.) of a patient while the patient is standing. A standing patient may straddle the coil arrangement such that all the coils of the coil arrangement are positioned under the lower abdominal region of the patient. Alternatively, a patient may sit (i.e., with the patient's feet not touching the ground or a platform below) on the coil arrangement. All of the coils may be positioned under the lower abdominal region of the sitting patient as well.

Figure 2:
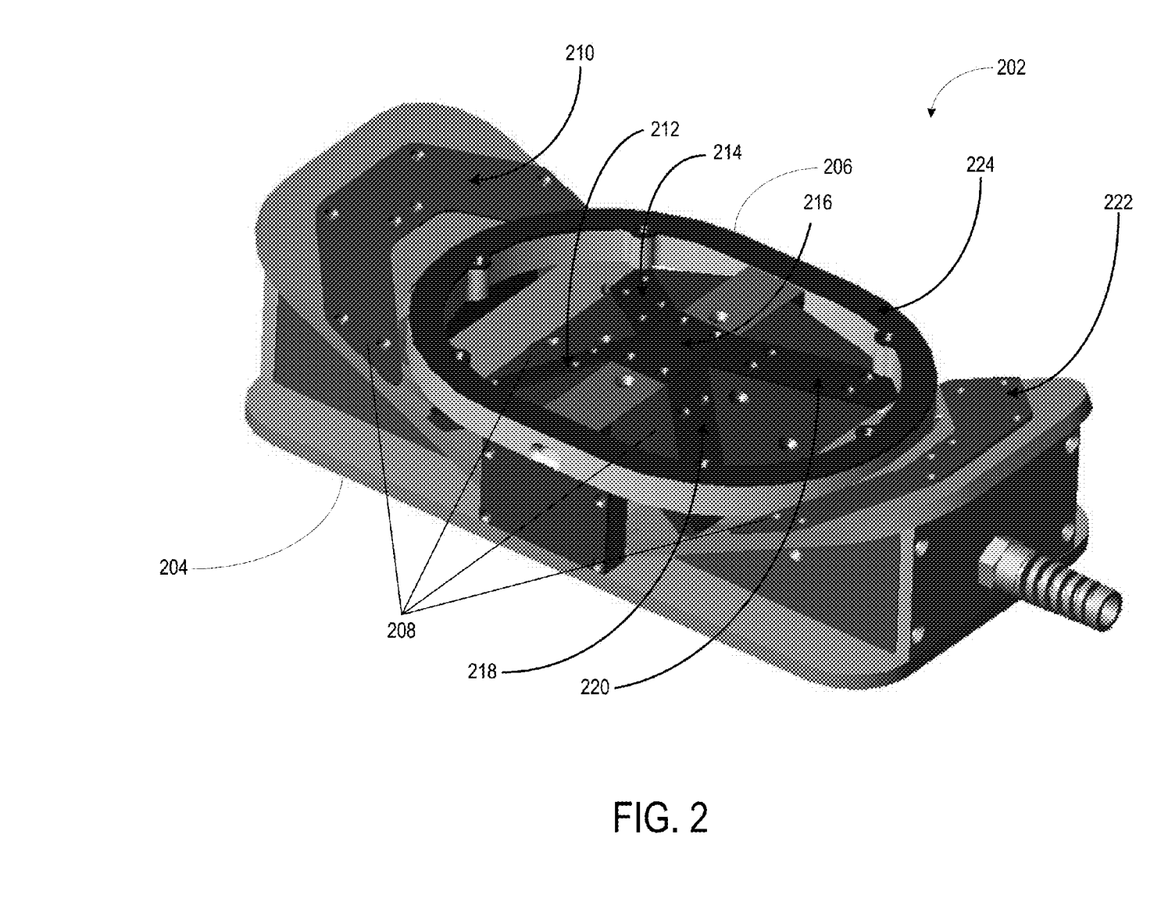
FIG. 2 illustrates an exemplary contoured quadrature coil arrangement according to aspects of this disclosure.

FIG. 2 illustrates an exemplary contoured quadrature coil arrangement 202 according to aspects of this disclosure. In particular, FIG. 2 is a perspective view of the quadrature coil arrangement 202 and the mechanical base 204 onto which the arrangement is placed.

In one embodiment, the contoured quadrature coil arrangement 202 includes a loop coil 206 resting on the top of the base or frame 204. The loop coil 206 may be substantially planar, extends about half the length of the base/frame 204, and extends about the full width of the base/frame 204. In other examples, the loop coil 206 may extend more than half the length and less than the full width of the base/frame 204, though it is preferable that the loop coil 206 not extend beyond the length or width of the frame. However, in some examples, the loop coil 206 may extend beyond the base/frame 204, though the manner in which such loop coil 206 is fastened to the base/frame is slightly different (e.g., alternate locations for screws, etc.).

The contoured quadrature coil arrangement 202 may also include an angled butterfly coil 208, the surface of which may be visible. In some examples, the angled butterfly coil 208 may be made of one or more segments. In other examples, the angled butterfly coil 208 may be a single continuous coil. Even the continuous coil may be thought of as having segments. For example, the angled butterfly coil 208 may include a central segment and two outer segments. The central segment may have a substantially intersectional (e.g., similar to the letter "X") shape (e.g., from a top down view) or pyramidal shape (e.g., from a side view). The side segments may each have an arc shape, each with a curve facing towards the center segment. In combination, the segments may appear to form a Figure-8.

In some examples, the continuous coil may include two or more breaks for input and an output connections to the coil. The breaks may further include capacitive interconnects in order to make a resonant circuit. The input and output connections may be symmetrically positioned. Preferably, an output connection may be at a break at one of the outer segments of the contoured butterfly coil 208.

In some examples, the central segment may itself be segmented into two segments, a front segment and a back segment. An input and/or output may be connected at a break between segments.

The Figure-8 formation of the angled butterfly coil 208 effectively forms two adjacent rings. The diameter of these rings may be substantially equal to one another (e.g., within about an inch). The diameter may be selected such that the coils have a far enough range of penetration (i.e., a far enough field of view) above the coils yet are small enough to maintain an optimum signal to noise ratio at the distance of the anatomy of interest (e.g., such that the scan provides a readable image). In some examples, the diameter of each ring may be about 5 inches to about 6 inches.

As mentioned above, the center of the angled butterfly coil 208 may be elevated in order to increase the intensity of the field of the coils at the depth of the anatomy of interest. Raising the center of the angled butterfly coil 208 effectively squashes a large coil into a relatively small horizontal space (compared to a flat or substantially planar butterfly coil), thereby retaining the benefits of scanning with a large coil (i.e., increased penetration) without entirely sacrificing the strength of the vector fields produced by the coil.

FIGS. 4A-4E illustrate various examples 402-410 demonstrating the benefit of raising the center of the angled butterfly coil 208 within the contoured quadrature coil arrangement 202 according to aspects of the disclosure. The examples 402-410 are not precise or to scale representations of the fields of view of the coils, and are only meant to be illustrative of the general concept of how raising the center of the butterfly coil improves the range of view of the coil arrangement.

Figure 4A:
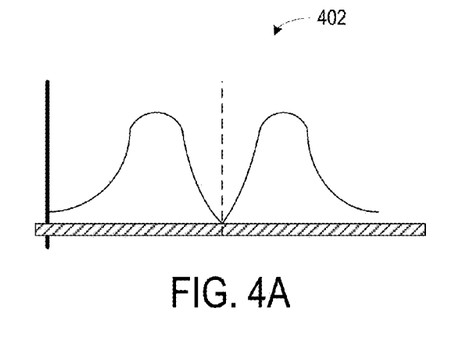
FIGS. 4A-4E illustrate various examples demonstrating the benefit of raising the center of the disclosed angled butterfly coil within the contoured quadrature coil arrangement according to aspects of the disclosure.

Example 402 depicts a field of view of a planar ring coil (at z=0). The field vector strength in the z-axis for the ring coil has a parabolic shape. Example 402 depicts this parabolic shape at a cross-sectional midpoint of the ring coil, where the field of view is greatest over the center of the ring coil and shrinks over the sides of the coil.

Figure 4B:
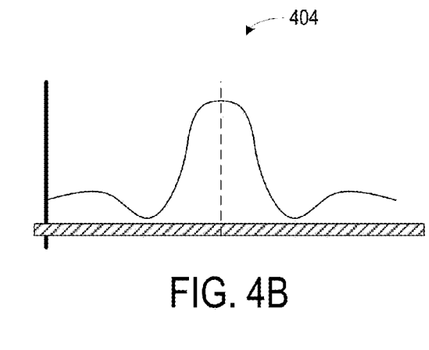
Figure 4C:
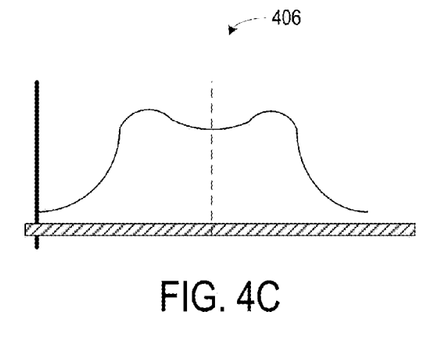

Example 404 depicts a field of view of a traditional butterfly coil. At the points above the two loops of the coil, the x-axis (horizontal) field of view is the strongest. The field vectors are slightly weaker at the center point above the standard butterfly coil.

When the planar ring coil is combined with the standard butterfly coil, an anatomy of interest may be viewed by both the ring coil and the butterfly coil (as in the standard quadrature arrangement). Effectively, the butterfly coil helps to fill out the gaps (i.e., blind spots) in the field of view of the ring coil due to the different direction of the field vectors used by the butterfly coil to view the anatomy of interest at the depth of interest (i.e., the distance above the butterfly coil or planar ring coil at which the anatomy of interest is positioned).

As mentioned above, in order to raise the field of view of the coil arrangement, the diameter of the coils may be increased. However, this is problematic because increasing the diameter of the coils will disperse the received resonance signal, reducing the signal-to-noise ratio at a given point, and thus resulting in a reduced clarity of the MRI image. The present disclosure instead contemplates extending the field of view of the coil arrangement along the z-axis (i.e., above the coils and perpendicular to the magnetic field vector) by creating a contoured butterfly coil having a raised center, which thereby enlarges the overall diameter of the butterfly coil while occupying the same amount of space horizontally.

Figure 4D:
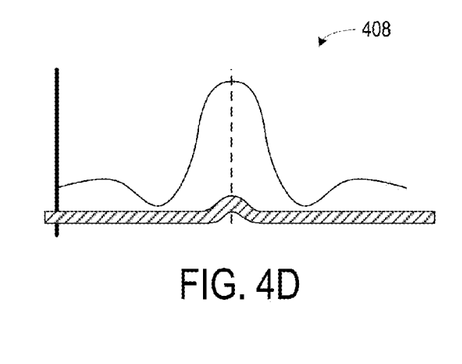
Figure 4E:
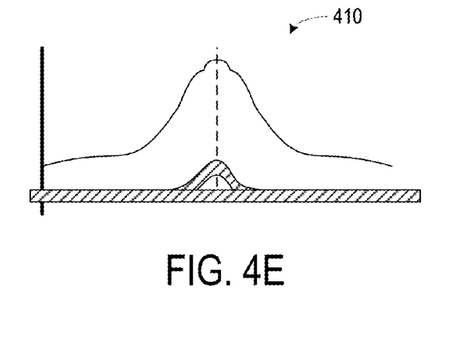

Examples 408-410 illustrate how the field of view of the disclosed contoured quadrature coil arrangement may be affected by extending the center of the angled butterfly coil upward along the z-axis. The extended range of the angled butterfly coil may result in the farthest point within the view of the contoured quadrature coil arrangement being directly above the arrangement, as opposed to a point slightly lateral to the point directly above the center of the coil arrangement (as illustrated in Example 404).

Although the angled butterfly coil may extend in a plane above the plane of the ring coil, in some examples of the disclosure, the angled butterfly coil may extend upwards but remain below the plane of the ring coil. In some further examples, the center point of the angled butterfly coil may be approximately within, or slightly lateral to, the plane of the ring coil, as illustrated in FIG. 2. While extending the angled butterfly coil is beneficial for the reasons described above, placing the center point of the angled butterfly coil above the plane of the ring coil may force the target anatomy of a patient farther away from the ring coil, thereby affecting the overall clarity of the scanning image. Alternatively, by placing the center point of the angled butterfly coil within or below the plane of the ring coil, the patient may be capable of sitting directly on top of the angled butterfly coil while the target anatomy remains in the plane, or just slightly above the plane of the ring coil, thereby providing an optimal imaging clarity.

Figure 3:
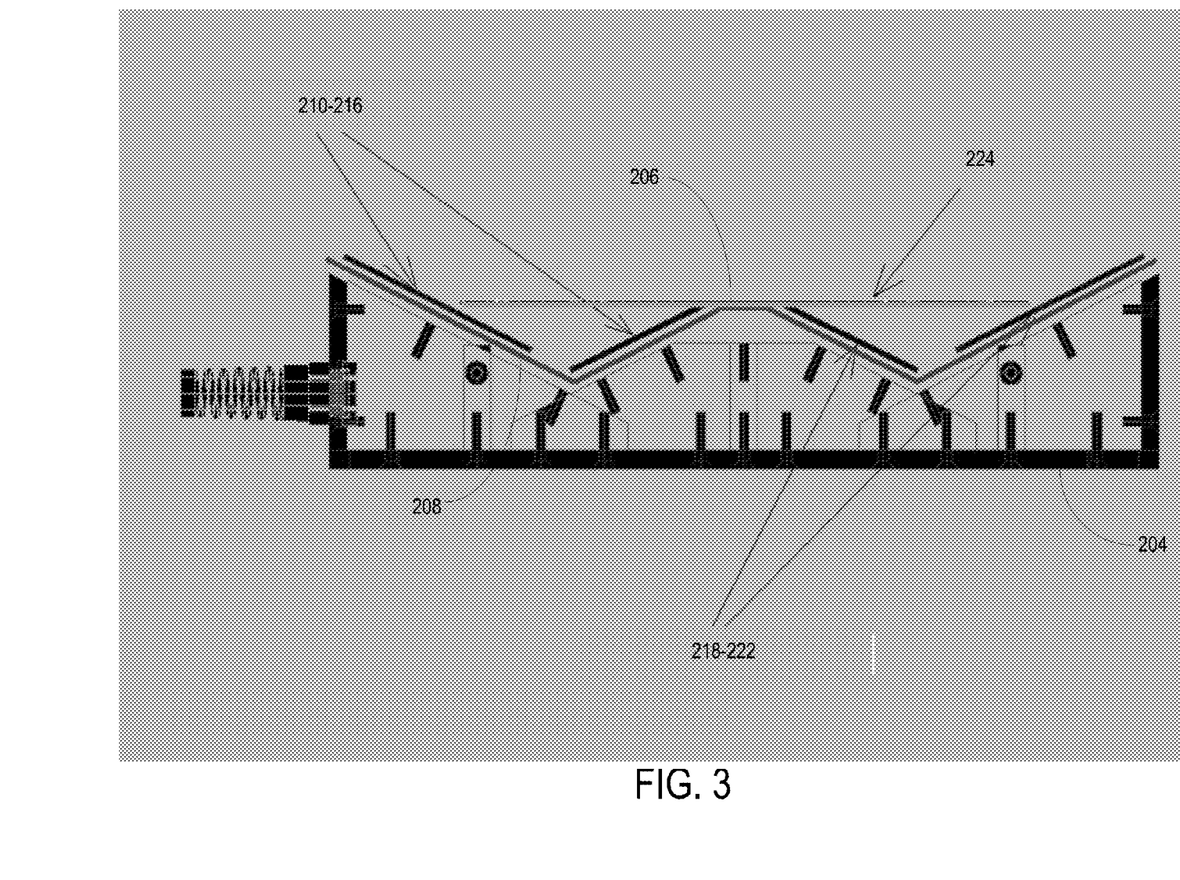
FIG. 3 illustrates a sectional view of the exemplary quadrature coil arrangement shown in FIG. 2, further showing a cross-section of the coils and base at the midpoint of the arrangement according to aspects of the disclosure.

In the same manner that the angled butterfly coil may be raised at the center, the present disclosure also contemplates raising the butterfly coil along each of its sides. FIG. 3 illustrates the exemplary quadrature coil arrangement 202 shown in FIG. 2, further showing a cross-section of the coils 206-208 and base 204 at the midpoint of the arrangement according to aspects of the disclosure. FIG. 3 illustrates that the angled butterfly coil 208 may be covered by various surfaces 210-216 to support a patient. FIG. 3 further illustrates that a surface 224 of the ring coil 206 may also be exposed to support a patient.

As with the field of view at the center point of the angled butterfly coil 208, raising the ends of the angled butterfly coil 208 may further squeeze a large coil loop into a smaller horizontal space In other examples of the disclosure, the side segments of the angled butterfly coil 208 may be lowered such that they are in plane with or slightly below the ring coil 206 in order to not interfere with a patient's ability to sit directly above the ring coil 206. Lowering the ends of the angled butterfly coil 208 may be accomplished by reducing the slope of the incline of the angled butterfly coil 208 on each end, shortening the overall length of the angled butterfly coil 208, or combinations thereof.

One or more segments of the angled butterfly coil 208 may be raised such that they are within a predetermined distance of an anatomy of interest of a patient. For example, the one or more segments may be raised such that they are as close to the anatomy of interest as possible. As such, the outer segments of the angled butterfly coil 208 may be raised or varied to different amounts in various embodiments of the disclosure, depending on the shape (e.g., wide or thin bone structure) of a patient for which the contoured quadrature coil arrangement 202 is designed. Nonetheless, as mentioned above, even if the butterfly coil outer segments are not flush against the patient, the contoured quadrature coil arrangement 202 still provides a significantly improved (i.e., extended) field of view for lower abdominal imaging. Thus, the shape of the contoured quadrature coil arrangement 202 has been molded and configured to approximate a saddle to achieve a close fit to a patient's anatomy.

As in the '209 Patent, the ring coil 206 has a coil vector that is substantially perpendicular to the magnetic field vector of the magnetic flux generator 104, and the angled butterfly coil 208 may have a coil vector that is substantially parallel to the base of the contoured quadrature coil arrangement 202, but orthogonal to the coil vector of the ring coil 206. By tilting the outer segments of the angled butterfly coil 208 upwards and towards the center of the contoured quadrature coil arrangement 202, the RF arc path between the two loops of the angled butterfly coil 208 is shortened and the RF field strength between the loops within the angled butterfly coil 208 may be increased, providing for greater imaging clarity.

FIG. 2 and FIG. 3 illustrate several holes for fastening the contoured quadrature coil arrangement 202 to the base 204. Screws or other fasteners (e.g., nails, bolts, etc.) may be inserted or secured into these or similarly placed holes in order fasten the contoured quadrature coil arrangement 202 to the base 204, and/or the base 204 to the seat 166 or bench on which the patient 154 may sit in order to be scanned/imaged.

FIG. 2 and FIG. 3 also illustrate that one or more surfaces 210-222, such as thin plastic plates, may cover the contoured butterfly coil 208. It may be uncomfortable for a patient to sit directly on top of the contoured butterfly coil 208, even with some padding in between. The plating, which is shown in FIG. 3 as four segments (but labeled as 210-222), may include several individual plates drilled or fastened into or onto the base/frame 204 to cover the track in which the resonant coil wires are placed. In FIG. 2, the outer segments of the butterfly coil may each be covered by an arc-shaped plate 210, 222, and the middle segment may be covered by an additional five plates 212-220 (four sloped 212-214,218-220 and one flat 216 plate between the four sloped plates). The ring coil may be covered by a donut-shaped circular plate 224. In other examples, the plates 210-222 may be divided into more segments (e.g., each outer segment of the angled butterfly coil 208 being covered by two half-arc shaped plates). Each plate 210-224 may be $\frac{1}{16}$ inch thick PVC or another sturdy smooth material that provides sufficient protection for the coils 206-208 and sufficient comfort to a patient 154 sitting on the plates 210-224 such that the patient 154 cannot feel either coil 206-208 (though the patient will feel the plating).

Though not pictured, the contoured quadrature coil arrangement 202 may be coupled to a preamplifier circuit to boost signal strength of the RF signal emitted by the coils 206-208 without significantly degrading the signal to noise ratio (SNR) of the received resonance signals. Preferably, the preamplifier is kept remote from the base 204. In other examples, the preamplifier may be attached/affixed to the base 204.

The disclosed quadrature coil arrangement 202 may be used in an upright scanner. For example, as discussed above, the quadrature coil arrangement 202 may be included in the seat 166 of a patient support 106. The patient 154 may then sit on top of or straddle the seat 166. For example, with reference to FIG. 3, a patient 154 that is sitting on top of or straddling the illustrated contoured quadrature coil arrangement 202 would be facing either to the left or the right of the illustration, with the left and right sides of the patient 154 extending out of the cross-sectional plane of the figure. In such an example, the portion of the patient 154 that is desired to be imaged may be aligned with the center of the contoured quadrature coil arrangement 202 (i.e., the midpoint of the cross-sectional view) in order to improve the imaging quality.

The coils 206-208 may be between about 5 inches and about 6 inches in width, and about 12 inches in length, giving the array a length about twice as long as its width. Additionally, the quadrature coil arrangement 202 may have an overall height of about 2 inches to about three inches (e.g., measured from the lowest point of the angled butterfly coil 208 along the z-axis to the uppermost point of the angled butterfly coil 208 along the z-axis). The base 204 may add up to about an extra inch or two of height to the arrangement.

The ring coil 206 may be shaped so as not to interfere with a patient's ability to sit on the protruding portion of the angled butterfly coil 208. In some embodiments, the ring coil 206 may be circular in shape. Alternatively, the loop coil 206 may be oval in shape.

The contoured quadrature coil arrangement 202 and base 204 may be padded to improve comfort for a patient 154 sitting on top of the coil arrangement. Additionally, the selected material for the padding may not be subject to heating upon activation of the coils 206-208. For example, the contoured quadrature coil arrangement 202 may be covered by a thin foam or other covering (e.g., closed-cell foam). The covering may be thick enough to provide some measure of conform for the patient 154 yet thin enough that the target imaging area is not significantly distanced from the coils 206-208. In some examples, the covering may be about an eighth of an inch thick.

In this manner, the disclosed contoured quadrature coil arrangement 202 provides increased clarity in the image of an anatomy of a patient. In particular, the angled butterfly coil 208 permits the contoured quadrature coil arrangement 202 to be placed closer to the patient, which results in the contoured quadrature coil arrangement 202 being closer to nuclei of the patient that are emitting resonance signals. Accordingly, the received signals are stronger are less noisy, which results in a clearer image of the anatomy of the patient.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An apparatus for magnetic resonance imaging, comprising:
   a magnet defining a patient-receiving space between first and second side walls that extend vertically from a floor and having a static magnetic field with a field vector in a substantially horizontal direction from the first side wall to the second side wall;
   a patient support configured to support a patient in the patient-receiving space, said patient support further comprising an upper surface configured to receive the patient in a sitting position;
   a contoured quadrature coil antenna arrangement configured to receive a signal from the patient disposed within the patient-receiving space, the contoured quadrature coil antenna arrangement being affixed to said patient support and comprising:
   a first antenna that is oriented parallel to the upper surface of the patient support, the first antenna being substantially planar and substantially circular; and
   a second antenna having a front outer section, an inner section, and a back outer section, the front outer section being oriented diagonally from a plane of the first antenna such that a first portion of the front outer section is disposed above the plane of the first antenna and a second portion of the front outer section is disposed below the plane of first antenna, the back outer section being oriented diagonally from the plane of the first antenna such that a first portion of the back outer section is disposed above the plane of the first antenna and a second portion of the back outer section is disposed below the plane of first antenna, wherein planes of the front and back outer sections are angled with respect to each other, and the inner section having intersecting segments and disposed along or below the plane of the first antenna.

2. The apparatus of claim 1, wherein the first antenna has a first coil vector, the second antenna has a second coil vector, and the first coil vector and the second coil vector are transverse with respect to the field vector of the magnet.

3. The apparatus of claim 1, wherein the contoured quadrature coil arrangement is disposed within a plane perpendicular to a horizontal axis of the static magnetic field.

4. The apparatus of claim 1, further comprising an elevator configured to raise and lower said patient support relative to said magnet while said patient support is holding the patient in an upright orientation so as to position any part of the patient within said patient-receiving space.

5. The apparatus of claim 1, wherein the second antenna comprises a plurality of discontinuous segments.

6. The apparatus of claim 5, wherein the discontinuous segments comprise:
   a central segment corresponding to the inner section of the second antenna; and
   a plurality of outer segments, the plurality of outer segments corresponding to the front outer section and the back outer section of the second antenna.

7. The apparatus of claim 6, wherein the central segment is discontinuous and comprises a front segment and a back segment.

8. The apparatus of claim 1, wherein the second antenna comprises a plurality of segments so as to be continuous.

9. An contoured quadrature coil antenna arrangement comprising:
- a first antenna that is substantially planar and substantially circular; and
- a second antenna having a front outer section, an inner section, and a back outer section, the front outer section being oriented diagonally from the plane of the first antenna such that a first portion of the front outer section is disposed above the plane of the first antenna and a second portion of the front outer section is disposed below the plane of first antenna, the back outer section being oriented diagonally from the plane of the first antenna such that a first portion of the back outer section is disposed above the plane of the first antenna and a second portion of the back outer section is disposed below the plane of first antenna, wherein planes of the front and back outer sections are angled with respect to each other, and the inner section having intersecting segments and disposed along or below the plane of the first antenna.

10. The contoured quadrature coil antenna arrangement of claim 9, wherein the first antenna has a first coil vector, the second antenna has a second coil vector, and the first coil vector and the second coil vector are orthogonal to each other.

11. The contoured quadrature coil antenna arrangement of claim 10, wherein the contoured quadrature antenna arrangement is configured to be disposed within a plane such that the first coil vector is perpendicular to a horizontal axis of a static magnetic field emitted by a magnet.

12. The contoured quadrature coil antenna arrangement of claim 9, wherein the contoured quadrature antenna coil arrangement is configured to be disposed within an enclosure mounted to an elevator configured to raise and lower a patient support relative to a magnet while the patient support is holding a patient in an upright orientation so as to position any part of the patient within a patient-receiving space.

13. The contoured quadrature coil antenna arrangement of claim 9, wherein the second antenna comprises a plurality of discontinuous segments.

14. The contoured quadrature coil antenna arrangement of claim 13, wherein the discontinuous segments comprise:
- a central segment corresponding to the inner section of the second antenna; and
- a plurality of outer segments, the plurality of outer segments corresponding to the front outer section and the back outer section of the second antenna.

15. The contoured quadrature coil antenna arrangement of claim 14, wherein the central segment is discontinuous and comprises a front segment and a back segment.

16. The contoured quadrature coil antenna arrangement of claim 9, wherein the second antenna comprises a plurality of segments so as to be continuous.

\* \* \* \* \*